US012570813B2

(12) United States Patent
Fang et al.

(10) Patent No.: US 12,570,813 B2
(45) Date of Patent: Mar. 10, 2026

(54) POLYMER FILM FOR BIOSENSOR AND PREPARATION METHOD THEREFOR

(71) Applicant: SHENZHEN SISENSING TECHNOLOGY CO., LTD., Shenzhen (CN)

(72) Inventors: Junfei Fang, Shenzhen (CN); Mingsong Han, Shenzhen (CN)

(73) Assignee: SHENZHEN SISENSING TECHNOLOGY CO., LTD., Shenzhen (CN)

( * ) Notice: Subject to any disclaimer, the term of this patent is extended or adjusted under 35 U.S.C. 154(b) by 676 days.

(21) Appl. No.: 18/000,134

(22) PCT Filed: Apr. 29, 2021

(86) PCT No.: PCT/CN2021/091224
§ 371 (c)(1),
(2) Date: Nov. 29, 2022

(87) PCT Pub. No.: WO2021/238577
PCT Pub. Date: Dec. 2, 2021

(65) Prior Publication Data
US 2023/0242719 A1     Aug. 3, 2023

(30) Foreign Application Priority Data

May 29, 2020    (CN) ......................... 202010479527.2

(51) Int. Cl.
C08J 5/18      (2006.01)
C08L 39/08     (2006.01)
A61B 5/145     (2006.01)

(52) U.S. Cl.
CPC ................. *C08J 5/18* (2013.01); *C08L 39/08* (2013.01); *A61B 5/14532* (2013.01);
(Continued)

(58) Field of Classification Search
None
See application file for complete search history.

(56) References Cited

FOREIGN PATENT DOCUMENTS

CN      102260663 A     11/2011
CN      102757538 A     10/2012
(Continued)

OTHER PUBLICATIONS

Hydroxymethyl chitosan (Year: 2025).*
(Continued)

*Primary Examiner* — Peter A Salamon
(74) *Attorney, Agent, or Firm* — AVEK IP, LLC

(57) ABSTRACT

Some embodiments of the disclosure provide a polymer film used for a biosensor. The polymer film has a three-dimensional network structure formed by a natural high-molecular polymer and a synthetic high-molecular polymer by a plurality of crosslinking modes. The three-dimensional network structure includes a chemically crosslinked network and a reversible physically crosslinked network, the chemically crosslinked network being formed by covalent bond crosslinking and the reversible physically crosslinked network being formed by ionic bond crosslinking. The chemically crosslinked network has covalent bond crosslinking between the synthetic high-molecular polymers and covalent bond crosslinking between the natural high-molecular polymer and the synthetic high-molecular polymer. The physically crosslinked network has ionic bond crosslinking between natural high-molecular polymers.

6 Claims, 4 Drawing Sheets

------- Synthetic high-molecular polymer
········· Natural high-molecular polymer
● Covalent bond crosslinking node
▲ Ionic bond crosslinking node

(52) U.S. Cl.
CPC ........ *C08J 2339/08* (2013.01); *C08J 2405/08* (2013.01); *C08J 2471/02* (2013.01); *C08L 2203/16* (2013.01); *C08L 2205/03* (2013.01); *C08L 2312/00* (2013.01)

(56) References Cited

FOREIGN PATENT DOCUMENTS

| | | | |
|---|---|---|---|
| CN | 103013014 A | | 4/2013 |
| CN | 102260663 B | * | 6/2013 |
| CN | 103446897 A | | 12/2013 |
| CN | 103013014 B | * | 12/2014 |
| CN | 109251449 A | | 1/2019 |
| CN | 109705370 A | | 5/2019 |
| CN | 111518298 A | | 8/2020 |

OTHER PUBLICATIONS

International Search Report for PCT/CN2021/091224 issued by CNIPA (China National Intellectual Property Administration) on Jul. 14, 2021.

* cited by examiner

Synthetic high-molecular polymer

Natural high-molecular polymer

Covalent bond crosslinking node

Ionic bond crosslinking node

POLYMER FILM FOR BIOSENSOR AND PREPARATION METHOD THEREFOR

CROSS REFERENCE TO RELATED APPLICATIONS

This application is the United State national stage entry under 37 U.S.C. 371 of PCT/CN2021/091224, filed on Apr. 29, 2021, which claims priority to Chinese application number 202010479527.2, filed on May 29, 2020, the disclosure of which are incorporated by reference herein in their entireties.

FIELD OF THE DISCLOSURE

The disclosure relates generally to the field of biosensors. More specifically, the disclosure relates to polymer films for biosensors and preparation methods therefor.

BACKGROUND

Biosensors are analytical devices that combine biological materials, biologically derived materials, or biomimetic materials closely with optical, electrochemical, temperature, piezoelectric, magnet, or micromechanical physicochemical sensors or sensing microsystems. They may often be used to rapidly detect some specific chemicals in the human body, such as glucose, urea, uric acid, and a series of amino acid compounds.

Taking an implantable current sensor in vivo as an example, a working electrode substantially includes a sensing layer in direct contact with an electrode conductive layer, and a film layer on the outermost side of the sensing layer, for example, for a glucose sensor. A film on the outermost side of an electrode is used to control a glucose concentration reaching a sensing layer, so that there is a fixed concentration difference in the glucose concentration inside and outside the film layer. As such, the sensing layer may detect a higher glucose concentration before saturation. However, the working electrode which is usually subjected to an external force during the implantation into the body and long-term immersion in a physiological environment easily causes damage, cracking, peeling, and other problems of the film layer on the outermost side of the working electrode, which in turn affects the inspection performance and biosafety performance.

SUMMARY

The following presents a simplified summary of the invention in order to provide a basic understanding of some aspects of the invention. This summary is not an extensive overview of the invention. It is not intended to identify critical elements or to delineate the scope of the invention. Its sole purpose is to present some concepts of the invention in a simplified form as a prelude to the more detailed description that is presented elsewhere.

In some embodiments, the disclosure provides a polymer film used for a biosensor. The polymer film has a three-dimensional network structure formed by a natural high-molecular polymer and a synthetic high-molecular polymer via a plurality of crosslinking modes. The three-dimensional network structure includes a chemically crosslinked network and a reversible physically crosslinked network, the chemically crosslinked network being formed by covalent bond crosslinking and the reversible physically crosslinked network being formed by ionic bond crosslinking. The chemically crosslinked network has covalent bond crosslinking between the synthetic high-molecular polymers and covalent bond crosslinking between the natural high-molecular polymer and the synthetic high-molecular polymer. The physically crosslinked network has ionic bond crosslinking between the natural high-molecular polymers. Both the natural high-molecular polymer and the synthetic high-molecular polymer are hydrophilic polymers. The natural high-molecular polymer includes at least one item selected from the group consisting of chitosan and derivatives thereof, alginic acid and derivatives thereof, hyaluronic acid and derivatives thereof, and cellulose and derivatives thereof.

Optionally, in the physically crosslinked network, metal ions are dynamic crosslinking points, and the metal ions includes at least one item selected from the group consisting of calcium ions, magnesium ions, aluminum ions, copper ions, iron ions, barium ions, zinc ions, sodium ions, strontium ions, chromium ions, platinum ions, lead ions, cobalt ions, cadmium ions, and nickel ions.

Optionally, ionic bond crosslinking is formed through a crosslinking agent in the physically crosslinked network, the crosslinking agent including at least one item selected from the group consisting of calcium chloride, magnesium chloride, ferric chloride, copper chloride, zinc chloride, barium phosphate, barium chloride, aluminum chloride, and sodium sulfate.

Optionally, the chemically crosslinked network is formed by crosslinking at least one item selected from the group consisting of active esters, epoxides, and sulfates by covalent bond crosslinking.

Optionally, in the polymer film, the chemically crosslinked network is configured as a primary network to provide rigidity, and the physically crosslinked network is configured as a secondary network to provide toughness.

Optionally, in the polymer film, a mass fraction of the natural high-molecular polymer is from 1% to 20%, and a mass fraction of the synthetic high-molecular polymer is from 80% to 99%.

Optionally, in the polymer film, the mass fraction of the natural high-molecular polymer is from 3% to 15%, and the mass fraction of the synthetic high-molecular polymer is from 85% to 97%.

Optionally, a molecular weight of the natural high-molecular polymer is from 1,000 Da to 500,000 Da, and a molecular weight of the synthetic high-molecular polymer is from 50,000 Da to 500,000 Da.

Optionally, the natural high-molecular polymer has polar groups, the polar groups including at least one item selected from the group consisting of hydroxyl, carboxymethyl, and carboxyl.

Optionally, both the natural high-molecular polymer and the synthetic high-molecular polymer are biocompatible.

In other embodiments, the disclosure provides a method for preparing a polymer film used for a biosensor including the following steps. Preparing a natural high-molecular polymer and a synthetic high-molecular polymer. Mixing the natural high-molecular polymer and the synthetic high-molecular polymer to form a mixture solution. Adding a crosslinking agent such that the natural high-molecular polymer and the synthetic high-molecular polymer form a three-dimensional crosslinked network, thereby obtaining the polymer film.

The three-dimensional crosslinked network includes a chemically crosslinked network and a reversible physically crosslinked network, the chemically crosslinked network being formed by covalent bond crosslinking and the reversible physically crosslinked network being formed by ionic bond crosslinking. The chemically crosslinked network has covalent bond crosslinking between the synthetic high-molecular polymers and covalent bond crosslinking between the natural high-molecular polymer and the synthetic high-molecular polymer. The physically crosslinked network has ionic bond crosslinking between the natural high-molecular polymers. Both the natural high-molecular polymer and the synthetic high-molecular polymer being hydrophilic polymers. The natural high-molecular polymer including at least one item selected from the group consisting of chitosan and derivatives thereof, alginic acid and derivatives thereof, hyaluronic acid and derivatives thereof, as well as cellulose and derivatives thereof.

Optionally, the mixture solution is formed by dissolving the natural high-molecular polymer and the synthetic high-molecular polymer in a cosolvent, the cosolvent including at least one item selected from the group consisting of ethanol, water, N,N-dimethylacrylamide, dimethyl sulfoxide, methanol, sulfolane, tetrahydrofuran, and dioxane.

Optionally, the crosslinking agent includes a first crosslinking agent for covalent bond crosslinking and a second crosslinking agent for ionic bond crosslinking, and the first crosslinking agent is added to the mixture solution to obtain a film solution.

Optionally, the cosolvent in the film solution is removed to obtain an intermediate film, the intermediate film is soaked in an aqueous solution of the second crosslinking agent, and the aqueous solution of the second crosslinking agent is a saturated solution.

Optionally, the intermediate film soaked in the aqueous solution of the second crosslinking agent is dried to obtain the polymer film.

Optionally, the first crosslinking agent includes at least one item selected from the group consisting of active esters, epoxides, and sulfates, and the second crosslinking agent includes at least one item selected from the group consisting of calcium chloride, magnesium chloride, ferric chloride, copper chloride, zinc chloride, barium phosphate, barium chloride, aluminum chloride, and sodium sulfate.

Optionally, the mass ratio of the first crosslinking agent to the synthetic high-molecular polymer is from 0.7% to 25%.

Optionally, the synthetic high-molecular polymer includes at least one item selected from the group consisting of a water-soluble polymer, a water-swellable homopolymer, and a water-swellable copolymer. The water-soluble polymer is selected from at least one of the group consisting of poly(N-vinylpyrrolidone), polyvinyl alcohol, polyvinylpyrrolidone, polyacrylamide, polyacrylic acid, poly(propylene glycol), sodium polystyrene sulfonate, polyethylene glycol, and polyethylene glycol-co-polypropylene glycol. The water-swellable homopolymer includes at least one item selected from the group consisting of polyurethane, polyethoxyethyl acrylate, polyethoxypropyl acrylate, poly-2-vinyl pyridine, poly-4-vinyl pyridine, polyhydroxyethyl methacrylate, and polyhydroxyethyl acrylate. The water-swellable copolymer includes at least one item selected from the group consisting of polyethylene glycol-block-polystyrene, polyacrylic acid-block-polystyrene, polyacrylic acid-co-polystyrene, polyacrylamide-block-polystyrene, poly-acrylamide-co-polystyrene, poly-2-vinylpyridine-block-polystyrene, poly-4-vinylpyridine-co-polystyrene, poly-2-vinylpyridine-co-polystyrene, and poly-4-vinylpyridine-block-polystyrene.

Optionally, when preparing the natural high-molecular polymer and the synthetic high-molecular polymer, the mass fraction of the natural high-molecular polymer is from 1% to 20%, and the mass fraction of the synthetic high-molecular polymer is from 80% to 99%.

Optionally, in the polymer film, the chemically crosslinked network is configured as a primary network to provide rigidity, and the physically crosslinked network is configured as a secondary network to provide toughness.

In some embodiments, the present disclosure provides a polymer film used for a biosensor. The polymer film has a three-dimensional network structure and is formed from a natural high-molecular polymer and a synthetic high-molecular polymer by a plurality of crosslinking modes. The three-dimensional network structure includes a chemically crosslinked network formed by covalent bond crosslinking and a reversible physically crosslinked network formed by ionic bond crosslinking. The chemically crosslinked network has covalent bond crosslinking between the synthetic high-molecular polymers and covalent bond crosslinking between the natural high-molecular polymer and the synthetic high-molecular polymer, and the physically crosslinked network has ionic bond crosslinking between the natural high-molecular polymers.

The natural high-molecular polymer and the synthetic high-molecular polymer are both hydrophilic polymers, and the natural high-molecular polymer is at least one selected from the group consisting of chitosan and derivatives thereof, alginic acid and derivatives thereof, hyaluronic acid and derivatives thereof, as well as cellulose and derivatives thereof. In the present disclosure, the chemically crosslinked network formed by covalent bond crosslinking may synergize with the reversible physically crosslinked network formed by ionic bond crosslinking to enhance the tensile resistance of the polymer film, and polar groups are increased by the natural high-molecular polymer to improve the adhesion property of the polymer film.

Optionally, in the physically crosslinked network, metal ions are used as dynamic crosslinking points, and the metal ions are at least one of the group consisting of calcium ions, magnesium ions, aluminum ions, copper ions, iron ions, barium ions, zinc ions, and sodium ions. Therefore, the formation of the reversible physically crosslinked network may be facilitated.

Optionally, the chemically crosslinked network is formed from at least one of active esters, epoxides, and sulfates by covalent bond crosslinking. Therefore, the formation of the chemically crosslinked network formed by covalent bond crosslinking may be facilitated.

Optionally, the natural high-molecular polymer is selected from at least one of the group consisting of chitosan, carboxymethyl chitosan, hydroxyethyl chitosan, chitosan sodium, alginic acid, sodium alginate, hyaluronic acid, sodium hyaluronate, cellulose, cellulose acetate, sodium carboxymethyl cellulose, hydroxyethyl cellulose, hydroxypropyl methyl cellulose. Therefore, the formation of the physically crosslinked network may be facilitated.

Optionally, the synthetic high-molecular polymer is selected from at least one of the group consisting of a water-soluble polymer, a water-swellable homopolymer, and a water-swellable copolymer. The water-soluble polymer is selected from at least one of the group consisting of poly (N-vinylpyrrolidone), polyvinyl alcohol, polyvinylpyrrolidone, polyacrylamide, polyacrylic acid, poly(propylene glycol), sodium polystyrene sulfonate, polyethylene glycol, and polyethylene glycol-co-polypropylene glycol. The water-swellable homopolymer is selected from at least one of the group consisting of polyurethane, polyethoxyethyl acrylate, polyethoxypropyl acrylate, poly-2-vinyl pyridine, poly-4-vinyl pyridine, polyhydroxyethyl methacrylate, and polyhydroxyethyl acrylate. The water-swellable copolymer is selected from at least one of the group consisting of polyethylene glycol-block-polystyrene, polyacrylic acid-block-polystyrene, polyacrylic acid-co-polystyrene, polyacrylamide-block-polystyrene, polyacrylamide-co-polystyrene, poly-2-vinylpyridine-block-polystyrene, poly-4-vinylpyridine-co-polystyrene, poly-2-vinylpyridine-co-polystyrene, and poly-4-vinylpyridine-block-polystyrene. Therefore, both the covalent bond crosslinking between the synthetic high-molecular polymers and the covalent bond crosslinking with the natural high-molecular polymer may be facilitated.

Optionally, a mass fraction of the natural high-molecular polymer is from 1% to 20%, and a mass fraction of the synthetic high-molecular polymer is from 80% to 99%. Therefore, the tensile resistance of the polymer film may be easily improved.

Optionally, a mass fraction of the natural high-molecular polymer is from 10% to 30%, and a mass fraction of the synthetic high-molecular polymer is from 70% to 90%. Therefore, the tensile resistance of the polymer film may be easily improved.

Optionally, a mass fraction of the natural high-molecular polymer is from 3% to 15%, and a mass fraction of the synthetic high-molecular polymer is from 85% to 97%. Therefore, the tensile resistance of the polymer film may be easily improved.

Optionally, a mass fraction of the natural high-molecular polymer is from 5% to 10%, and a mass fraction of the synthetic high-molecular polymer is from 90% to 95%. Therefore, the tensile resistance of the polymer film may be easily improved.

Optionally, a molecular weight of the natural high-molecular polymer is from 1,000 Da to 500,000 Da, and a molecular weight of the synthetic high-molecular polymer is from 50,000 Da to 500,000 Da. Therefore, the film-forming property of the polymer film may be easily improved.

Optionally, a molecular weight of the natural high-molecular polymer is from 1,000 Da to 50,000 Da, and a molecular weight of the synthetic high-molecular polymer is from 80,000 Da to 300,000 Da. Therefore, the film-forming property of the polymer film may be easily improved.

Optionally, a molecular weight of the natural high-molecular polymer is from 1,000 Da to 5,000 Da, and a molecular weight of the synthetic high-molecular polymer is from 100,000 Da to 200,000 Da. Therefore, the film-forming property of the polymer film may be easily improved.

In other embodiments, the disclosure provides a preparation method for a polymer film used for a biosensor. The preparation method includes the following steps. Preparing a natural high-molecular polymer and a synthetic high-molecular polymer, the natural high-molecular polymer and the synthetic high-molecular polymer are both hydrophilic polymers, and the natural high-molecular polymer is selected from at least chitosan and derivatives thereof, alginic acid and derivatives thereof, hyaluronic acid and derivatives thereof, as well as cellulose and derivatives thereof. Mixing the natural high-molecular polymer and the synthetic high-molecular polymer to form a mixture solution. Adding a crosslinking agent such that the natural high-molecular polymer and the synthetic high-molecular polymer form a three-dimensional crosslinked network, thereby obtaining the polymer film.

The three-dimensional network structure includes a chemically crosslinked network formed by covalent bond crosslinking and a reversible physically crosslinked network formed by ionic bond crosslinking. The chemically crosslinked network has covalent bond crosslinking between the synthetic high-molecular polymers and covalent bond crosslinking between the natural high-molecular polymer and the synthetic high-molecular polymer, and the physically crosslinked network has ionic bond crosslinking between the natural high-molecular polymers. In this case, the polymer film with enhanced tensile resistance may be obtained from the chemically crosslinked network formed by covalent bond crosslinking and the reversible physically crosslinked network formed by ionic bond crosslinking, and polar groups may be increased by the polymer film prepared from the natural high-molecular polymer to improve the adhesion property of the polymer film.

Optionally, the mixture solution is formed by dissolving the natural high-molecular polymer and the synthetic high-molecular polymer through a cosolvent, the cosolvent is selected from at least one of the group consisting of ethanol, water, N,N-dimethylacrylamide, dimethyl sulfoxide, methanol, sulfolane, tetrahydrofuran, and dioxane. Therefore, the polymer film may be prepared by dissolving the natural high-molecular polymer and the synthetic high-molecular polymer.

Optionally, a mass fraction of the natural high-molecular polymer is from 1% to 20%, and a mass fraction of the synthetic high-molecular polymer is from 80% to 99%. Therefore, the polymer film with better tensile resistance may be prepared.

Optionally, the crosslinking agent includes a first crosslinking agent for covalent bond crosslinking and a second crosslinking agent for ionic bond crosslinking, the first crosslinking agent is at least one of the group consisting of active esters, epoxides and sulfates, and the second crosslinking agent is at least one of the group consisting of calcium chloride, magnesium chloride, ferric chloride, copper chloride, zinc chloride, barium phosphate, barium chloride, aluminum chloride, and sodium sulfate. Therefore, the polymer film may be prepared by a plurality of crosslinking modes.

Optionally, a mass ratio of the first crosslinking agent to the synthetic high-molecular polymer is from 0.7% to 25%. Therefore, the progress of the crosslinking reaction may be facilitated.

Optionally, the synthetic high-molecular polymer is selected from at least one of the group consisting of a water-soluble polymer, a water-swellable homopolymer, and a water-swellable copolymer. The water-soluble polymer is selected from at least one of the group consisting of polyN-vinylpyrrolidone, polyvinyl alcohol, polyvinylpyrrolidone, polyacrylamide, polyacrylic acid, poly(propylene glycol), sodium polystyrene sulfonate, polyethylene glycol, and polyethylene glycol-co-polypropylene glycol. The water-swellable homopolymer is selected from at least one of the group consisting of polyurethane, polyethoxyethyl acrylate, polyethoxypropyl acrylate, poly-2-vinyl pyridine, poly-4-vinyl pyridine, polyhydroxyethyl methacrylate, and polyhydroxyethyl acrylate. The water-swellable copolymer is selected from at least one of the group consisting of polyethylene glycol-block-polystyrene, polyacrylic acid-block-polystyrene, polyacrylic acid-co-polystyrene, polyacrylamide-block-polystyrene, polyacrylamide-co-polystyrene, poly-2-vinylpyridine-block-polystyrene, poly-4-vinylpyridine-co-polystyrene, poly-2-vinylpyridine-co-polystyrene, and poly-4-vinylpyridine-block-polystyrene. Therefore, the crosslinking between the synthetic high-molecular polymers and the natural high-molecular polymer may be facilitated.

BRIEF DESCRIPTION OF THE DRAWINGS

Illustrative embodiments of the present disclosure are described in detail below with reference to the attached drawing figures.

7

Figure 1:
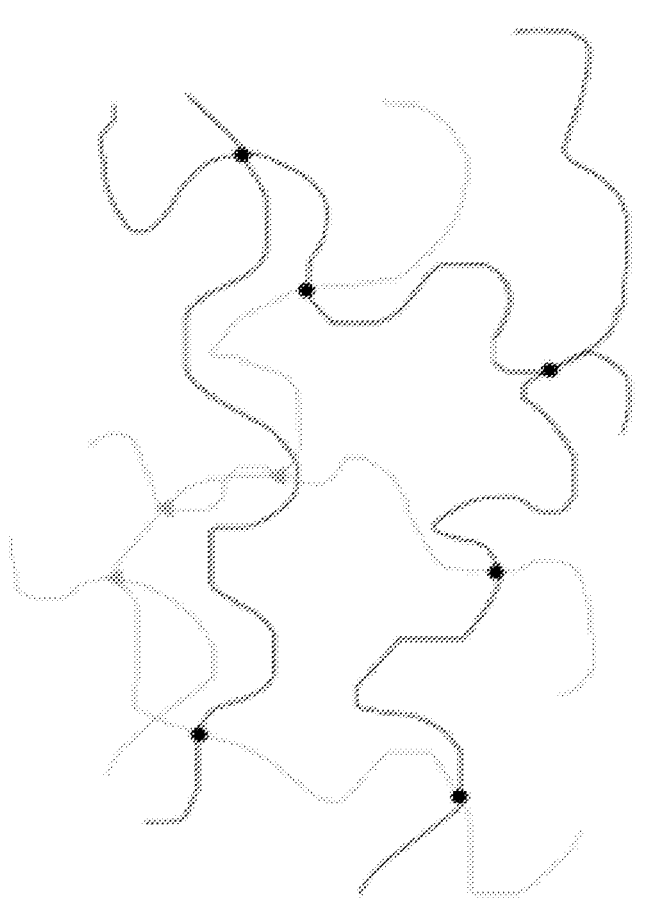

FIG. 1 shows a structure of a polymer film used for a biosensor according to an embodiment of the present disclosure.

Figure 2:
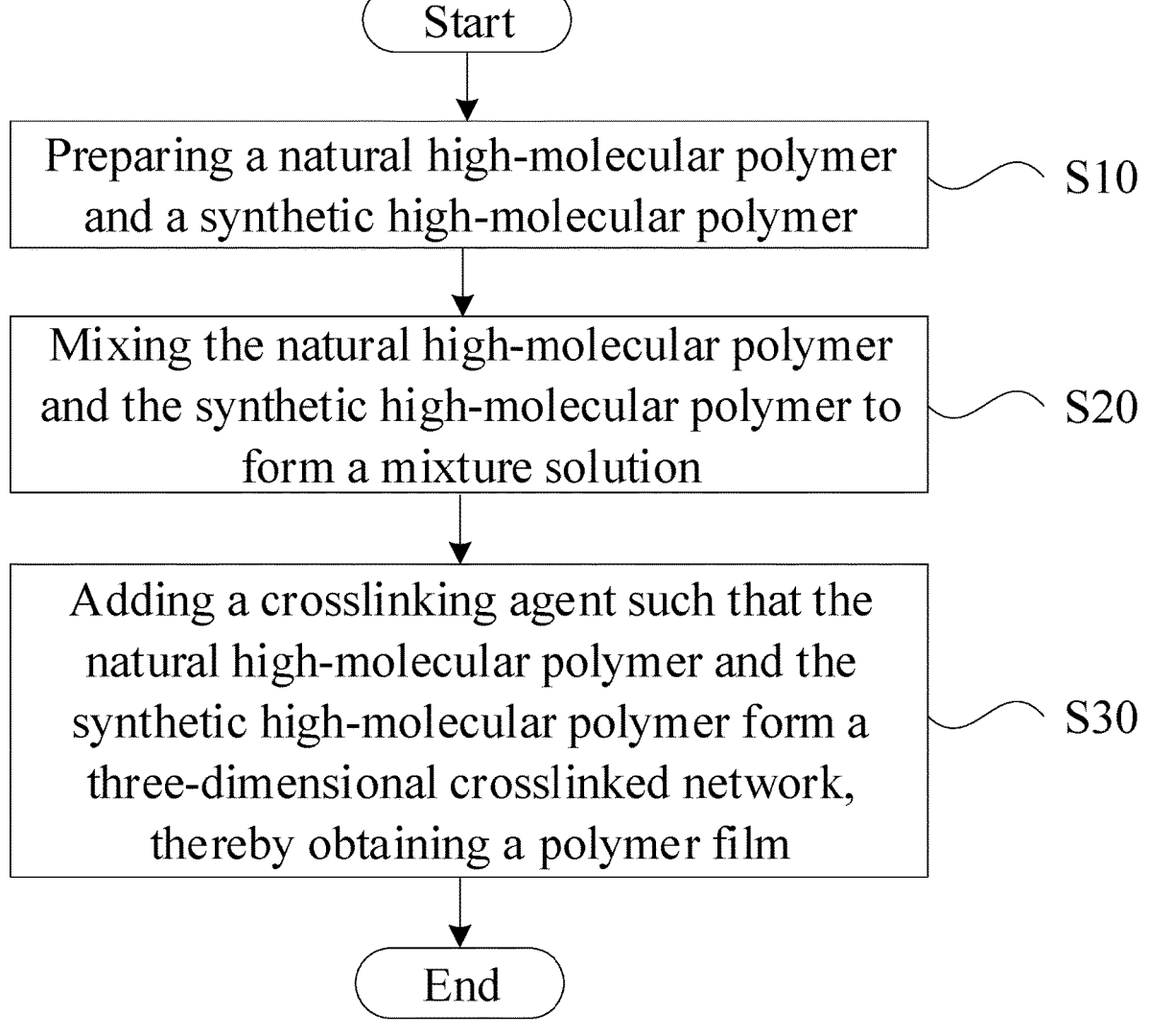

FIG. 2 shows a method for preparing a polymer film for a biosensor according to an embodiment of the present disclosure.

Figure 3:
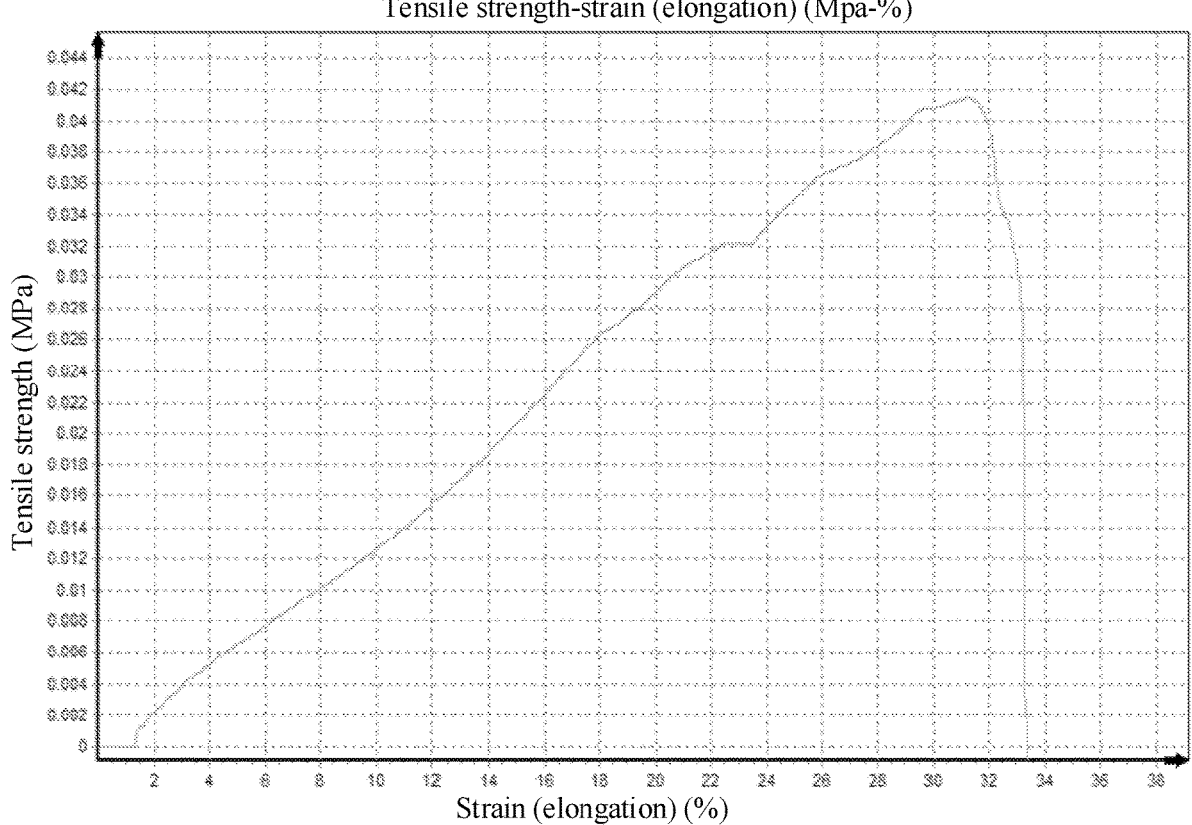

FIG. 3 is a diagram showing test results of the tensile resistance of a polymer film prepared in an embodiment of the present disclosure.

Figure 4:
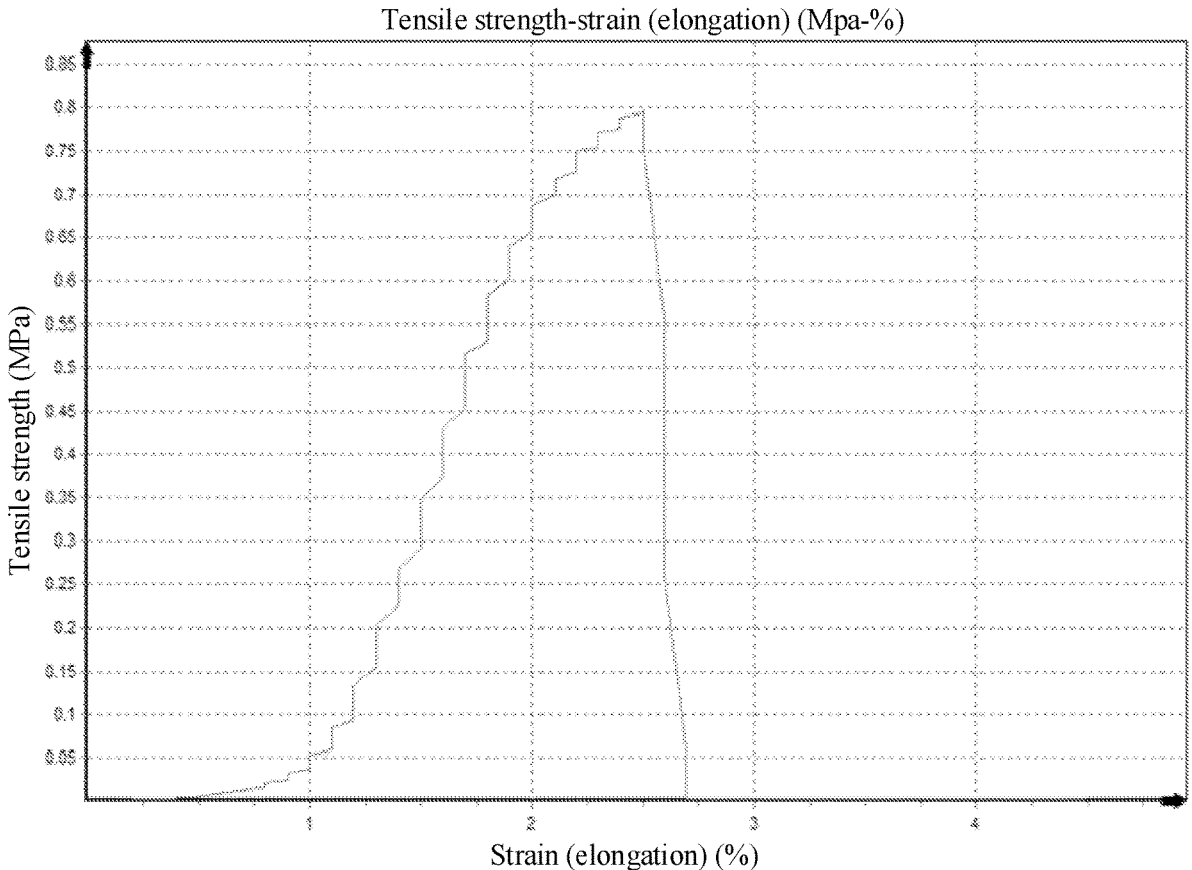

FIG. 4 is a diagram showing test result of the tensile resistance of a polymer film prepared in a comparative example of the present disclosure

DETAILED DESCRIPTION

The following describes some non-limiting exemplary embodiments of the invention with reference to the accompanying drawings. The described embodiments are merely a part rather than all of the embodiments of the invention. All other embodiments obtained by a person of ordinary skill in the art based on the embodiments of the disclosure shall fall within the scope of the disclosure.

Hereinafter, preferred embodiments of the present disclosure will be described in detail with reference to the accompanying drawings. In the following description, the same reference numerals are assigned to the same components, and repeated descriptions are omitted. In addition, the drawings are only schematic diagrams, and the ratios in dimensions of the components, the shapes of the components, and the like may be different from those of the actual ones.

In the present disclosure, a polymer film used for a biosensor may be referred to as a polymer film for short, and a preparation method for the polymer film used for the biosensor may be referred to as a preparation method for short. In addition, the polymer film involved by the present disclosure may be applied to electrochemical sensors (e.g., a biosensor) for the detection of small molecular chemicals in tissues in vivo and physiological environments, such as a blood glucose monitoring device (e.g., a glucose sensor) for monitoring blood glucose, a uric acid monitoring device (e.g., a uric acid sensor) for monitoring uric acid, and a cholesterol monitoring device (e.g., a cholesterol sensor) for detecting cholesterol.

The polymer film involved by the present disclosure has biocompatibility, and may be used as a diffusion-limiting film applied in biosensors (such as glucose sensors) to play a role in diffusion control, thereby improving the response performance of the biosensors, that is, expanding the response linear range of the biosensors, and reducing the interference from non-detecting substances, and further slowing down the attenuation of sensitivity. In addition, the polymer film involved by the present disclosure may be applied to biosensors (e.g., glucose sensors), which may slow down the loss of bioactive molecules (e.g., glucose enzymes) on the biosensors.

In addition, when the polymer film is applied to biosensors (e.g., glucose sensors) as a diffusion-limiting film, the desired diffusion-controlling performance may be obtained by controlling the thickness, adjusting the components, and the like.

FIG. 1 shows a structure of a polymer film used for a biosensor according to an example of the present disclosure.

In this embodiment, the polymer film used for the biosensor may be formed from a natural high-molecular polymer and a synthetic high-molecular polymer. Additionally, as shown in FIG. 1, the polymer film may be formed by a plurality of crosslinking modes, such as covalent bond crosslinking and ionic bond crosslinking. In addition, the polymer film may have a three-dimensional network structure.

In some examples, the three-dimensional network structure may include a chemically crosslinked network formed by covalent bond crosslinking. In addition, the chemically crosslinked network may have covalent bond crosslinking between the synthetic high-molecular polymers and covalent bond crosslinking between the natural high-molecular polymer and the synthetic high-molecular polymer. That is, the chemically crosslinked network may have covalent bond crosslinking between the synthetic high-molecular polymers. The chemically crosslinked network may have covalent bond crosslinking between the natural high-molecular polymer and the synthetic high-molecular polymer.

In some examples, the three-dimensional network structure may include a reversible physically crosslinked network formed by ionic bond crosslinking. Moreover, the physically crosslinked network may have ionic bond crosslinking between the natural high-molecular polymers. Therefore, the chemically crosslinked network formed by covalent bond crosslinking may synergize with the reversible physically crosslinked network formed by ionic bond crosslinking to enhance the tensile resistance of the polymer film, and polar groups are increased by the natural high-molecular polymer to improve the adhesion property of the polymer film.

In some examples, the natural high-molecular polymer and the synthetic high-molecular weight polymer may both be hydrophilic polymers. In addition, the natural high-molecular polymer may be selected from at least one of the group consisting of chitosan and derivatives thereof, alginic acid and derivatives thereof, hyaluronic acid and derivatives thereof, as well as cellulose and derivatives thereof.

In this embodiment, the interaction between the polymers is weakened by using a plurality of crosslinking modes in order to reduce a glass transition temperature of the polymer film and improve the tensile resistance of the polymer film. The chemically crosslinked network formed by covalent bond crosslinking may synergize with the reversible physically crosslinked network formed by ionic bond crosslinking to enhance the tensile resistance of the polymer film, and polar groups may be increased by the natural high-molecular polymer to improve the adhesion property of the polymer film. In addition, weakening the interaction and lowering the glass transition temperature may facilitate enhancement of the adhesion property of the polymer film.

In some examples, the polymer film may be formed by crosslinking the natural high-molecular polymer with the synthetic high-molecular polymer. Specifically, the polymer film may be a composite material formed from a natural high-molecular polymer and a synthetic high-molecular polymer by a plurality of crosslinking modes (i.e., a composite crosslinking mode).

In some examples, a mass fraction of the natural high-molecular polymer may be from 1% to 20%. A mass fraction of the synthetic high-molecular polymer may be from 80% to 99%. Therefore, the tensile resistance of the polymer film may be easily improved. In addition, if the mass fraction of the natural high-molecular polymer is too high or too low, the mechanical property of the polymer film is easily reduced, which in turn easily leads to poor tensile resistance of the polymer film.

In some examples, a mass fraction of the natural high-molecular polymer may be 1%, 2%, 3%, 4%, 5%, 6%, 7%, 8%, 9%, 10%, 11%, 12%, 13%, 14%, 15%, 16%, 17%, 18%, 19%, or 20%.

In some examples, a mass fraction of the synthetic high-molecular polymer may be 80%, 81%, 82%, 83%, 84%, 85%, 86%, 87%, 88%, 89%, 90%, 91%, 92%, 93%, 94%, 95%, 96%, 97%, 98%, or 99%.

In some examples, a mass fraction of the natural high-molecular polymer may be from 3% to 15%, and a mass fraction of the synthetic high-molecular polymer may be from 85% to 97%. Therefore, the tensile resistance of the polymer film may be easily improved.

In some examples, optionally, a mass fraction of the natural high-molecular polymer may be from 5% to 10%, and a mass fraction of the synthetic high-molecular polymer may be from 90% to 95%. Therefore, the tensile resistance of the polymer film may be easily improved.

In other examples, a mass fraction of the natural high-molecular polymer may be from 10% to 30%, and a mass fraction of the synthetic high-molecular polymer may be from 70% to 90%. Therefore, the tensile resistance of the polymer film may be easily improved. For example, the mass fraction of the natural high-molecular polymer may be 10%, 12%, 15%, 17%, 20%, 25%, or 30%, and the mass fraction of the synthetic high-molecular polymer may be 70%, 72%, 75%, 78%, 80%, 85%, or 90%.

In some examples, both the natural high-molecular polymer and the synthetic high-molecular weight polymer may be hydrophilic polymers. Therefore, the natural high-molecular polymer and the synthetic high-molecular polymer may have better compatibility. In addition, both the natural high-molecular polymer and the synthetic high-molecular polymer may have biocompatibility, and may thus be applied to a working electrode of an implantable biosensor.

In some examples, the natural high-molecular polymer may be a polysaccharides high-molecular compound. In addition, in the present disclosure, the natural high-molecular polymer may refer to a natural high-molecular compound and a semi-natural high-molecular compound formed by chemical modification of the natural high-molecular compound.

In some examples, as described above, the natural high-molecular polymer may be selected from at least one of the group consisting of chitosan and derivatives thereof, alginic acid and derivatives thereof, hyaluronic acid and derivatives thereof, as well as cellulose and derivatives thereof. In addition, examples of the present disclosure are not limited thereto. For example, the natural high-molecular polymer may be selected from the group consisting of starch and derivatives thereof, chitin and derivatives thereof, lignin and derivatives thereof, xylan and derivatives thereof, and the like.

In some examples, the natural high-molecular polymer may be selected from at least one of the group consisting of chitosan, carboxymethyl chitosan, hydroxyethyl chitosan, chitosan sodium, alginic acid, sodium alginate, hyaluronic acid, sodium hyaluronate, cellulose, cellulose acetate, sodium carboxymethyl cellulose, hydroxyethyl cellulose, and hydroxypropyl methyl cellulose. Therefore, the formation of the physically crosslinked network may be facilitated.

In some examples, the natural high-molecular polymer may have polar groups, such as hydroxyl, carboxymethyl, or carboxyl, etc. Therefore, the adhesion property of the polymer film may be easily improved.

In some examples, a molecular weight of the natural high-molecular polymer may be from 1,000 Da to 500,000 Da. Therefore, the film-forming property of the polymer film may be easily improved. For example, the molecular weight of the natural high-molecular polymer may be 1,000 Da, 1,100 Da, 1,200 Da, 1,300 Da, 1,400 Da, 1,500 Da, 1,600 Da, 1,700 Da, 1,800 Da, 1,900 Da, 2,000 Da, 2,100 Da, 2,200 Da, 2,300 Da, 2,400 Da, 2,500 Da, 2,600 Da, 2,700 Da, 2,800 Da, 2,900 Da, 3,000 Da, 3,500 Da, 4,000 Da, 5,000 Da, 8,000 Da, 10,000 Da, 50,000 Da, 100,000 Da or 500,000 Da.

In some examples, a molecular weight of the natural high-molecular polymer may be from 1,000 Da to 50,000 Da. Therefore, the film-forming property of the polymer film may be easily improved. In other examples, optionally, a molecular weight of the natural high-molecular polymer may be from 1,000 Da to 5,000 Da. Therefore, the film-forming property of the polymer film may be further improved.

In some examples, the synthetic high-molecular polymer may be selected from at least one of the group consisting of a water-soluble polymer and a water-swellable polymer. Additionally, the water-swellable polymer may include a water-swellable homopolymer and a water-swellable copolymer. In other words, the synthetic high-molecular polymer may be selected from at least one of the group consisting of a water-soluble polymer, a water-swellable homopolymer and a water-swellable copolymer. Therefore, the covalent bond crosslinking of the synthetic high-molecular polymer may be facilitated.

In some examples, the water-soluble polymer may be selected from one least of the group consisting of polyN-vinylpyrrolidone, polyvinyl alcohol, polyvinylpyrrolidone, polyacrylamide, polyacrylic acid, polypropylene glycol, sodium polystyrene sulfonate, polyethylene glycol, and polyethylene glycol-co-polypropylene glycol. Therefore, not only the covalent bond crosslinking between the synthetic high-molecular polymers but also the covalent bond crosslinking with the natural high-molecular polymer may be facilitated.

In some examples, the water-swellable homopolymer may be selected from at least one of the group consisting of polyurethane, polyethoxyethyl acrylate, polyethoxypropyl acrylate, poly-2-vinylpyridine, poly-4-vinylpyridine, poly-hydroxyethyl methacrylate, and polyhydroxyethyl acrylate. Therefore, not only the covalent bond crosslinking between the synthetic high-molecular polymers but also the covalent bond crosslinking with the natural high-molecular polymer may be facilitated.

In some examples, the water-swellable copolymer may be selected from at least one of the group consisting of poly-ethylene glycol-block-polystyrene, polyacrylic acid-block-polystyrene, polyacrylic acid-co-polystyrene, polyacrylam-ide-block-polystyrene, polyacrylamide-co-polystyrene, poly-2-vinylpyridine-block-polystyrene, poly-4-vinylpyri-dine-co-polystyrene, poly-2-vinylpyridine-co-polystyrene, and poly-4-vinylpyridine-block-polystyrene. Therefore, not only the covalent bond crosslinking between the synthetic high-molecular polymers but also the covalent bond cross-linking with the natural high-molecular polymer may be facilitated.

In some examples, a molecular weight of the synthetic high-molecular polymer may be from 50,000 Da to 500,000 Da. Therefore, the film-forming property of the polymer film may be easily improved. For example, the molecular weight of the synthetic high-molecular polymer may be 50,000 Da, 60,000 Da, 70,000 Da, 80,000 Da, 90,000 Da, 100,000 Da, 110,000 Da, 120,000 Da, 130,000 Da, 140,000 Da, 150,000 Da, 160,000 Da, 170,000 Da, 180,000 Da, 190,000 Da, 200,000 Da, 250,000 Da, 300,000 Da, 400,000 Da or 500,000 Da.

In some examples, a molecular weight of the synthetic high-molecular polymer may be from 80,000 Da to 300,000 Da. Therefore, the film-forming property of the polymer film may be easily improved. In other examples, optionally, a molecular weight of the synthetic high-molecular polymer may be from 100,000 Da to 200,000 Da. Therefore, the film-forming property of the polymer film may be further improved.

Generally speaking, if the molecular weight of the synthetic high-molecular polymer is lower than 50,000 Da, the film-forming property of the polymer film is poor and thus not conducive to the coating of the polymer film. If the molecular weight of the synthetic high-molecular polymer is higher than 500,000 Da, the solubility of the synthetic high-molecular polymer is likely to deteriorate that may affect the film formation quality.

In some examples, as described above, the polymer film may have a three-dimensional network structure (see FIG. 1). The three-dimensional network structure may include a chemically crosslinked network. That is, the polymer film may include a chemically crosslinked network.

In other examples, the chemically crosslinked network may be formed by covalent bond crosslinking. Specifically, the chemically crosslinked network may be formed by covalent bond crosslinking between the natural high-molecular polymer and the synthetic high-molecular polymer and the covalent bond crosslinking between the synthetic high-molecular polymers.

In other words, the chemically crosslinked network may include covalent bond crosslinking between the natural high-molecular polymer and the synthetic high-molecular polymer and covalent bond crosslinking between the synthetic high-molecular polymers. In some examples, the covalent bond crosslinking between the synthetic high-molecular polymers may include covalent bond crosslinking between the synthetic high-molecular polymers and covalent bond crosslinking of the synthetic high-molecular polymer itself.

In other examples, the chemically crosslinked network may form covalent bond crosslinking via a crosslinking agent. The crosslinking agent may be, for example, at least one of active esters, epoxides, and sulfates. In other words, the chemically crosslinked network may be formed form at least one of active esters, epoxides, and sulfates by covalent bond crosslinking. Therefore, the formation of the chemically crosslinked network formed by covalent bond crosslinking may be facilitated.

In some examples, as described above, the three-dimensional network structure may include a physically crosslinked network. That is, the polymer film may include a physically crosslinked network. Therefore, the interaction between polymers (for example, between natural high-molecular polymers) in the polymer film may be weakened. In other examples, the physically crosslinked network may be formed by ionic bond crosslinking. Additionally, the physically crosslinked network may be reversible. Therefore, the polymer film may have a certain self-healing ability.

In some examples, the physically crosslinked network may be formed by ionic bond crosslinking between the natural high-molecular polymers. In other words, the physically crosslinked network may include ionic bond crosslinking between the natural high-molecular polymers. In other examples, the ionic bond crosslinking between the natural high-molecular polymers may include ionic bond crosslinking between the natural high-molecular polymers and ionic bond crosslinking of the natural high-molecular polymer itself.

In other examples, the physically crosslinked network may have dynamic crosslinking points. Therefore, the tensile resistance and the self-healing ability may be improved. In other examples, the physical crosslinking network having ion bond crosslinking may be formed by utilizing the complexing ability of the polysaccharides natural high-molecular polymer to metal ions.

In some examples, in the physically crosslinked network, the metal ions may be taken as dynamic crosslinking points. Therefore, the formation of a reversible physically crosslinked network may be facilitated. In addition, examples of the present disclosure are not limited thereto. For example, chitosan and derivatives thereof may be subjected to ionic bond crosslinking by using sodium tripolyphosphate.

In some examples, the metal ions may be at least one of the group consisting of calcium ions, magnesium ions, aluminum ions, copper ions, iron ions, barium ions, zinc ions, and sodium ions. In addition, the actual selection of the metal ions may be related to the actually used natural polymer. In addition, examples of the present disclosure are not limited thereto. For example, the metal ions may be strontium ions, chromium ions, platinum ions, lead ions, cobalt ions, cadmium ions, nickel ions, or the like.

In some examples, in the polymer film, the chemically crosslinked network may act as a primary network to provide rigidity and the physically crosslinked network may act as a secondary network to provide toughness, thereby enabling improved mechanical properties and enhanced tensile resistance.

Hereinafter, with reference to FIG. 2, a preparation method for a polymer film for a biosensor according to an example in this embodiment is described in detail. FIG. 2 shows a preparation method for a polymer film for the biosensor according to an example of the present disclosure.

In this embodiment, as shown in FIG. 2, the preparation method for the polymer film for the biosensor may include the following steps. Preparing a natural high-molecular polymer and a synthetic high-molecular polymer (step S10). Mixing the natural high-molecular polymer and the synthetic high-molecular polymer to form a mixture solution (step S20). Adding a crosslinking agent such that the natural high-molecular polymer and the synthetic high-molecular polymer form a three-dimensional crosslinked network, thereby obtaining the polymer film (step S30). The three-dimensional network structure may include a chemically crosslinked network and a physically crosslinked network.

In the preparation method for the polymer film for the biosensor in this embodiment, the polymer film with enhanced tensile resistance may be obtained from the chemically crosslinked network formed by covalent bond crosslinking and the reversible physically crosslinked network formed by ionic bond crosslinking, and polar groups may be increased by the polymer film prepared from the natural high-molecular polymer to improve the adhesion property of the polymer film.

In some examples, in step S10, the natural high-molecular polymer and the synthetic high-molecular polymer may be prepared as preparation raw materials. In some examples, in the preparation raw materials, a mass fraction of the natural high-molecular polymer may be from 1% to 20%, and a mass fraction of the synthetic high-molecular polymer may be from 80% to 99%. Therefore, the polymer film with better tensile resistance may be prepared.

In some examples, in step S10, the natural high-molecular polymer may be selected from at least one of the group consisting of chitosan, carboxymethyl chitosan, hydroxyethyl chitosan, chitosan sodium, alginic acid, sodium alginate, hyaluronic acid, sodium hyaluronate, cellulose, cellulose acetate, sodium carboxymethyl cellulose, hydroxyethyl cellulose, and hydroxypropyl methyl cellulose.

In some examples, in step S10, both the natural high-molecular polymer and the synthetic high-molecular weight polymer may be hydrophilic polymers. In addition, the natural high-molecular polymer may be selected from at least one of the group consisting of chitosan and derivatives thereof, alginic acid and derivatives thereof, hyaluronic acid and derivatives thereof, as well as cellulose and derivatives thereof.

In some examples, in step S10, the synthetic high-molecular polymer may be selected from at least one of the group consisting of a water-soluble polymer, a water-swellable homopolymer, and a water-swellable copolymer. The water-soluble polymer may be selected from at least one of the group consisting of poly N-vinylpyrrolidone, polyvinyl alcohol, polyvinylpyrrolidone, polyacrylamide, polyacrylic acid, polypropylene glycol, sodium polystyrene sulfonate, polyethylene glycol, and polyethylene glycol-co-polypropylene glycol. The water-swellable homopolymer may be selected from at least one of the group consisting of polyurethane, polyethoxyethyl acrylate, polyethoxypropyl acrylate, poly-2-vinyl pyridine, poly vinyl pyridine, polyhydroxyethyl methacrylate, and polyhydroxyethyl acrylate. The water-swellable copolymer may be selected from at least one of the group consisting of polyethylene glycol-block-polystyrene, polyacrylic acid-block-polystyrene, polyacrylic acid-co-polystyrene, polyacrylamide-block-polystyrene, polyacrylamide-co-polystyrene, poly-2-vinylpyridine-block-polystyrene, poly-4-vinylpyridine-co-polystyrene, poly-2-vinylpyridine-co-polystyrene, and poly-4-vinylpyridine-block-polystyrene. Therefore, the crosslinking between the synthetic high-molecular polymer and the natural high-molecular polymer may be facilitated.

In some examples, in step S10, a molecular weight of the natural high-molecular polymer may be from 1,000 Da to 500,000 Da, and a molecular weight of the synthetic high-molecular polymer may be from 50,000 Da to 500,000 Da. In addition, specific descriptions of the natural high-molecular polymer and the synthetic high-molecular polymer may refer to the above description of the polymer film used for the biosensor.

In some examples, in step S20, the mixture solution may be formed by dissolving the natural high-molecular polymer and the synthetic high-molecular polymer through a cosolvent. Therefore, the polymer film may be prepared by dissolving the natural high-molecular polymer and the synthetic high-molecular polymer. In the present disclosure, the cosolvent may refer to a solvent capable of dissolving both the natural high-molecular polymer and the synthetic high-molecular polymer.

In some examples, in step S20, the cosolvent may be selected from at least one of the group consisting of ethanol, water, N,N-dimethylacrylamide, dimethyl sulfoxide, methanol, sulfolane, tetrahydrofuran, and dioxane.

In some examples, in step S20, the mixture solution may be formed by respectively dissolving the natural high-molecular polymer and the synthetic high-molecular weight polymer through a cosolvent and then mixing. In other examples, in step S20, the natural high-molecular polymer and the synthetic high-molecular polymer may be dissolved together in the cosolvent. In addition, the well-mixed mixture solution may be obtained by stirring, ultrasonic processing, oscillation, or the like.

In some examples, in step S30, the three-dimensional network structure may include a chemically crosslinked network formed by covalent bond crosslinking. In addition, the chemically crosslinked network may have covalent bond crosslinking between the synthetic high-molecular polymers and covalent bond crosslinking between the natural high-molecular polymer and the synthetic high-molecular polymer.

In some examples, in step S30, the three-dimensional network structure may include a reversible physically crosslinked network formed by ionic bond crosslinking. Moreover, the physically crosslinked network may have ionic bond crosslinking between the natural high-molecular polymers.

In some examples, in step S30, as described above, a crosslinking agent may be added and reacted to obtain the polymer film. In other examples, in step S30, the crosslinking agent may include a first crosslinking agent for covalent bond crosslinking and a second crosslinking agent for ionic bond crosslinking. Therefore, the polymer film may be prepared by a plurality of crosslinking modes.

In some examples, the first crosslinking agent may be, for example, at least one of active esters, epoxides, and sulfates.

In some examples, the second crosslinking agent may be at least one of the group consisting of calcium chloride, magnesium chloride, ferric chloride, copper chloride, zinc chloride, barium phosphate, barium chloride, aluminum chloride, and sodium sulfate.

In some examples, in step S30, the first crosslinking agent may be added to the mixture solution to obtain a film solution. In addition, the well-mixed film solution may be obtained by stirring, ultrasonic processing, oscillation, or the like. In other examples, a mass ratio of the first crosslinking agent to the synthetic high-molecular polymer may be from 0.7% to 25%. Therefore, the progress of the crosslinking reaction may be facilitated.

In some examples, a mass ratio of the first crosslinking agent to the synthetic high-molecular polymer may be 0.7%, 0.8%, 0.9%, 1%, 1.1%, 1.2%, 1.3%, 1.4%, 1.5%, 1.6%, 1.7%, 1.8%, 1.9%, 2%, 2.2%, 2.4%, 2.6%, 2.8%, 3%, 3.5%, 4%, 4.5%, 5%, 10%, 15%, 20%, or 25%. In addition, for the purposes of promoting the crosslinking reaction and improving the tensile resistance of the polymer film, the mass ratio of the first crosslinking agent to the synthetic high-molecular polymer may be from 1.5% to 5%.

In some examples, in step S30, the cosolvent in the film solution may be removed to obtain an intermediate film. In some examples, in step S30, the cosolvent may be removed by volatilization. For example, an aqueous ethanol solution is used as the cosolvent, and may be volatilized in an ethanol atmosphere at room temperature.

In some examples, in step S30, the intermediate film may be soaked in an aqueous solution of the second crosslinking agent for a predetermined time. Therefore, the natural high-molecular polymer may be subjected to ionic bond crosslinking. In other examples, the predetermined time may be from 15 minutes to 45 minutes. Therefore, ionic bond crosslinking may be sufficiently performed.

In some examples, optionally, the aqueous solution of the second crosslinking agent may be a saturated solution. Therefore, the progress of the crosslinking reaction may be facilitated.

In some examples, in step S30, the intermediate film soaked in the aqueous solution of the second crosslinking agent may be taken out and dried to obtain the polymer film. In addition, drying may be performed at room temperature in a nitrogen or inert gas atmosphere.

In this embodiment, the specific description of the polymer film prepared by the preparation method may refer to the above description of the polymer film. According to the present disclosure, a polymer film for a biosensor, which has good tensile resistance and adhesion property, and therefore a preparation method may be provided.

In order to further illustrate the present disclosure, the polymer film for the biosensor provided by the present disclosure will be described in detail below with reference to an embodiment, and the beneficial effects achieved by the present disclosure will be fully described with reference to a comparative example.

FIG. 3 is a diagram showing a test result of the tensile resistance of a polymer film prepared in an embodiment of the present disclosure. FIG. 4 is a diagram showing a test result of the tensile resistance of a polymer film prepared in a comparative example of the present disclosure.

In the embodiments of the present disclosure, poly-4-vinyl pyridine is used as a synthetic high-molecular polymer, and carboxymethyl chitosan is used as a natural high-molecular polymer. 9 grams of poly-4-vinylpyridine and 1 grams of carboxymethyl chitosan are used as preparation raw materials (a total mass of 10 grams), and 0.5 grams of polyethylene glycol ethylene oxide is dissolved in 50 ml of water to form an aqueous solution as an aqueous solution of the first crosslinking agent for later use, and sodium sulfate is dissolved into a saturated aqueous solution as an aqueous solution of the second crosslinking agent for later use.

Embodiment

A synthetic high-molecular polymer is added to 50 ml of 80% aqueous ethanol solution, and subjected to ultrasonic processing and oscillation to obtain a synthetic high-molecular polymer solution. A natural high-molecular polymer is added to 50 ml of 80% aqueous ethanol solution and subjected to ultrasonic processing and oscillation to obtain a natural high-molecular polymer solution. The synthetic high-molecular polymer aqueous solution and the natural high-molecular polymer aqueous solution are then mixed evenly. Next, a first crosslinking agent aqueous solution is added and subjected to vortexed oscillation for 10 minutes to obtain a film solution, and the film solution is divided into two parts: a film solution A and a film solution B.

The film solution A is poured into a 20 mm×5 mm×1 mm dumbbell-shaped mold, and placed in an ethanol atmosphere to allow it to evaporate rapidly at room temperature for 24 hours to obtain an intermediate film. Next, the intermediate film layer is soaked in a saturated sodium sulfate aqueous solution at room temperature for 30 minutes, taken out and dried at room temperature to obtain a polymer film. The polymer film is then coated with dimethicone to keep the moisture of the polymer film stable. A tensile testing machine (brand: Precise Test, model: PT-501B-1) is used to test the tensile resistance of the polymer film. The test temperature is 25° C. and the tensile rate is 0.1 mm/s. The test results are shown in FIG. 3.

The film solution B is poured onto a 10 cm×3 cm×0.05 cm rectangular glass slide, and wrapped around with polytetrafluoroethylene to form a film solution tank having a thickness of 0.05 cm. The film solution tank is then placed in an ethanol atmosphere to make it volatilize rapidly at room temperature for 24 hours to obtain an intermediate film. The intermediate film is then soaked in a saturated sodium sulfate aqueous solution for 30 minutes at room temperature, taken out and dried at room temperature for 48 hours to obtain a polymer film. A surrounding Teflon frame is then removed and torn off by using silicone tweezers from the slide along the border of the polymer film. The adhesion property of the polymer film are determined according to the degree of peeling off, indicating the polymer film prepared in this embodiment is difficult to peel off from the glass slide.

Comparative Example

This comparative example differs from the above embodiment in that: the comparative example only uses poly-4-vinylpyridine as a preparation raw material, except that the same preparation and testing methods are used as the above embodiment. The test results of the tensile resistance are shown in FIG. 4, and the polymer film obtained in the comparative example is easily peeled off from the glass slide.

As may be seen from FIG. 3 and FIG. 4, the tensile elongation at break of the polymer film in the embodiment is 33.47%, and the elongation at break of the polymer film in the comparative example is 2.65%. It may thus be seen that the polymer film in the embodiment has remarkably enhanced tensile resistance than the polymer film in the comparative example, that is, the polymer film in the embodiment has better tensile resistance.

In addition, the polymer film in the embodiment is difficult to peel off from the glass slide, while the polymer film in the comparative example is easily peeled off from the glass slide. It may thus be seen that the polymer film in the embodiment has stronger adhesive property than that in the comparative example, and the polymer film in the embodiment has better adhesive property.

Various embodiments of the disclosure may have one or more of the following effects. In some embodiments, the polymer film prepared in the present disclosure has good tensile resistance and adhesion property. In other embodiments, the polymer film in the present disclosure has better adhesive property than traditional polymer films and is more difficult to peel off from the glass slide.

Although the present disclosure has been specifically described above with reference to the accompanying drawings and examples, it is to be understood that the above description does not limit the present disclosure in any form. Those skilled in the art may make modifications and changes of the present disclosure as required without departing from the essential spirit and scope of the present disclosure, and these modifications and changes all fall within the scope of the present disclosure.

Many different arrangements of the various components depicted, as well as components not shown, are possible without departing from the spirit and scope of the present disclosure. Embodiments of the present disclosure have been described with the intent to be illustrative rather than restrictive. Alternative embodiments will become apparent to those skilled in the art that do not depart from its scope. A skilled artisan may develop alternative means of implementing the aforementioned improvements without departing from the scope of the present disclosure.

It will be understood that certain features and subcombinations are of utility and may be employed without reference to other features and subcombinations and are contemplated within the scope of the claims. Unless indicated otherwise, not all steps listed in the various figures need be carried out in the specific order described.

What is claimed is:

1. A polymer film used for a biosensor, which is a diffusion-limiting film for controlling diffusion of a glucosidase enzyme, wherein:

the polymer film has a three-dimensional network structure formed by a natural high-molecular polymer and a synthetic high-molecular polymer via a plurality of crosslinking modes;

the three-dimensional network structure comprises a chemically crosslinked network and a reversible physically crosslinked network, the chemically crosslinked network being formed by covalent bond crosslinking and the reversible physically crosslinked network being formed by ionic bond crosslinking;

the chemically crosslinked network has covalent bond crosslinking between the synthetic high-molecular polymers and covalent bond crosslinking between the natural high-molecular polymer and the synthetic high-molecular polymer;

the physically crosslinked network has ionic bond crosslinking between the natural high-molecular polymers;

both the natural high-molecular polymer and the synthetic high-molecular polymer are hydrophilic polymers; and the natural high-molecular polymer is hydroxymethyl chitosan, and the synthetic high molecular polymer is poly-4-vinylpyridine.

2. The polymer film according to claim 1, wherein, in the physically crosslinked network:

metal ions are dynamic crosslinking points; and the metal ions comprises at least one of calcium ions, magnesium ions, aluminum ions, copper ions, iron ions, barium ions, zinc ions, and sodium ions.

3. The polymer film according to claim 1, wherein the chemically crosslinked network is formed by crosslinking at least one of active esters, epoxides, and sulfates by covalent bond crosslinking.

4. The polymer film according to claim 1, wherein:

a mass fraction of the natural high-molecular polymer is from 1% to 20%; and a mass fraction of the synthetic high-molecular polymer is from 80% to 99%.

5. The polymer film according to claim 4, wherein:

the mass fraction of the natural high-molecular polymer is from 3% to 15%; and the mass fraction of the synthetic high-molecular polymer is from 85% to 97%.

6. The polymer film according to claim 1, wherein:

a molecular weight of the natural high-molecular polymer is from 1,000 Da to 500,000 Da; and a molecular weight of the synthetic high-molecular polymer is from 50,000 Da to 500,000 Da.

* * * * *